United States Patent [19]
Yamamoto et al.

[11] 4,423,281
[45] Dec. 27, 1983

[54] PROCESS FOR PRODUCING CONJUGATED DIOLEFINS

[75] Inventors: Haruhisa Yamamoto; Nobuaki Yoneyama, both of Takaoka, Japan

[73] Assignee: Nippon Zeon Co. Ltd., Tokyo, Japan

[21] Appl. No.: 249,614

[22] Filed: Mar. 31, 1981

[30] Foreign Application Priority Data

Apr. 4, 1980 [JP] Japan ................................. 55-44137

[51] Int. Cl.$^3$ ........................... C07C 5/18; C07C 5/48
[52] U.S. Cl. .................................. 585/626; 585/622; 585/631; 502/212; 502/308; 502/311; 502/315
[58] Field of Search ....................... 585/626, 622, 631

[56] References Cited

U.S. PATENT DOCUMENTS

| | | | |
|---|---|---|---|
| 3,380,931 | 4/1968 | Ryland | 585/626 X |
| 3,801,670 | 4/1974 | Shiraishi et al. | 585/626 |
| 3,821,324 | 6/1974 | Bertus | 585/626 X |
| 3,925,498 | 12/1975 | Stadig | 585/626 X |
| 3,956,181 | 5/1976 | Grasselli et al. | 585/626 X |
| 4,035,418 | 7/1977 | Okata et al. | 585/626 X |

Primary Examiner—Robert V. Hines
Attorney, Agent, or Firm—Sherman & Shalloway

[57] ABSTRACT

In a process for producing a conjugated diolefin which comprises oxidatively dehydrogenating a monolefin having at least 4 carbon atoms in the vapor phase with molecular oxygen to form the corresponding conjugated diolefin; the improvement wherein the oxidative dehydrogenation is carried out in the presence of a catalyst having the general composition formula

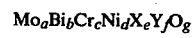
$Mo_aBi_bCr_cNi_dX_eY_fO_g$ wherein X represents at least one element selected from Li, Na, K, Rb, Cs, Tl and P, Y represents at least one element selected from Al, Ga, Zr, Pb, Nb, Ta, Hf and Mn, and a, b, c, d, e, f and g respectively represent the number of Mo, Bi, Cr, Ni, X, Y and O atoms, and when a=12, b=0.05–20, c=0.05–20, d=0.1–30, e=0.01–10, f=0.01–20, and g is the number of oxygen atoms which satisfies the atomic valences of the other elements.

7 Claims, No Drawings

PROCESS FOR PRODUCING CONJUGATED DIOLEFINS

This invention relates to a process for producing conjugated diolefins by oxidative dehydrogenation. More specifically, it relates to a process for producing a conjugated diolefin by oxidatively dehydrogenating a monolefin having at least 4 carbon atoms with molecular oxygen in the vapor phase to obtain the corresponding diolefin, which process is characterized by using a novel catalyst to obtain the final product efficiently.

A process is known for oxidatively dehydrogenating a monolefin having at least 4 carbon atoms such as n-butene or isopentene in the vapor phase with molecular oxygen in the presence of a catalyst to produce a conjugated diolefin (e.g., 1,3-butadiene or isoprene) corresponding to the monolefin.

For use in such a known process, multi-component catalysts consisting essentially of molybdenum, bismuth and iron are known to exhibit high activity (see, for example, U.S. Pat. Nos. 3,764,632, 3,801,670 and 3,932,551). These catalysts, however, vary greatly in activity depending upon the type of the isomers of the starting monolefin. For example, in the case of n-butene for production of butadiene, the catalyst activity varies greatly depending upon whether it is butene-1, trans-butene-2, or cis-butene-2. For this reason, when this type of catalyst system is applied to an isomeric mixture of a monolefin available industrially at low cost, the desired conjugated diolefin can be obtained only in very low yields.

Multi-component catalysts consisting essentially of molybdenum, bismuth and chromium have also been developed. One example of this type of catalyst comprises (1) molybdenum, (2) bismuth, (3) chromium and (4) nickel or cobalt as essential ingredients, and (5) an alkali metal, thallium, indium, etc., and (6) phosphorus, arsenic, antimony, etc. (U.S. Pat. No. 3,956,181). This catalyst system has the advantage of possessing excellent selectivity at high temperatures. Investigations of the present invention, however, have shown that this catalyst has the same defect as the aforesaid catalysts comprising molybdenum, bismuth and iron as essential ingredients, and also has a short active lifetime.

It is an object of this invention therefore to provide a process for producing a conjugated diolefin efficiently by discovering a catalyst which always has high activity whether the starting material is a single isomer of a monolefin, or an isomeric mixture of the same monolefin, namely irrespective of the constituents and proportions of the starting material.

The object of this invention is achieved by an improved process for producing a conjugated diolefin by oxidatively dehydrogenating a monolefin having at least 4 carbon atoms with molecular oxygen in the vapor phase, wherein the oxidative dehydrogenation reaction is carried out by using a catalyst having the general composition formula

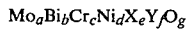

$$Mo_a Bi_b Cr_c Ni_d X_e Y_f O_g$$

wherein X represents at least one element selected from Li, Na, K, Rb, Cs, Tl and P, Y represents at least one element selected from Al, Ga, Zr, Pb, Nb, Ta, Hf and Mn, and a, b, c, d, e, f and g respectively represent the number of Mo, Bi, Cr, Ni, X, Y and O atoms, and when $a=12$, $b=0.05-20$, preferably 0.1–8, $c=0.05-20$, preferably 0.1–10, $d=0.1-30$, preferably 1–20, $e=0.01-10$, preferably 0.01–5, $f=0.01-20$, preferably 0.05–10, and g is the number of oxygen atoms which satisfies the atomic valences of the other elements.

The monolefin used as a starting material in this invention may be any of monolefins having at least 4 carbon atoms heretofore used in the synthesis of conjugated diolefins by oxidative dehydrogenation. Specific examples include butene-1, butene-2, pentene-1, pentene-2, 2-methylbutene-1, 2-methylbutene-2, 3-methylbutene-1, 2,3-dimethylbutene-1, and 2,3-dimethylbutene-2. These monolefins need not always to be used in isolated form, and may be used in the form of mixtures. For example, in the production of 1,3-butadiene, it is possible to use a fraction (to be referred to as "BBRR" hereinbelow) obtained by separating 1,3-butadiene and isobutylene from a $C_4$ fraction formed as a by-product in the cracking of naphtha, or a butene fraction formed by the dehydrogenation or oxidative dehydrogenation of n-butane as a starting material instead of highly pure butene-1 or butene-2. In such a case, an equivalent yield can be obtained to the case of using a single material of high purity. In the production of isoprene or 1,3-pentadiene, a fraction consisting of isopentene as a main ingredient or a fraction containing n-pentene as a main component can be used. Use of a $C_5$ monolefin fraction containing isopentene and n-pentene as main ingredients may yield isoprene and 1,3-pentadiene at the same time.

The structural characteristic of the catalyst used in this invention which is expressed by the above general composition formula is that it contains nickel, component X and component Y as essential ingredient. If cobalt is included instead of nickel, or the component X is not included, its catalytic activity is unexpectedly decreased. If the catalyst does not contain the component Y, the variations in catalytic activity depending upon the types of the isomers of monolefin, which is the defect of the conventional catalysts, cannot be avoided.

Catalysts in accordance with this invention in which the component X is K, Rb, Cs, Tl or P and the component Y is Al, Zr, Pb or Mn exhibit especially good performances. The component X and Y needs not to be composed of a single element, and may include two or more elements.

The catalyst in accordance with this invention can be prepared by various methods known in the art, for example, a method involving evaporation to dryness, a method involving mixing oxides, and a co-precipitation method. The materials used in catalyst preparation are not limited to the oxides of the individual elements, and may be any compounds of the individual element capable of forming the catalyst of this invention by calcination. Examples include salts such as the ammonium salts, nitrates, carbonates, organic acid salts, and halides, free acids, acid anhydrides, condensed acids, etc. Molybdenum-containing heteropolyacids such as phosphomolybdic acid or silicomolybdic acid, and their salts such as ammonium salts and metallic salts can also be used. Use of a silicon-containing compound such as silicomolybdic acid does not adversely affect the activity of the resulting catalyst.

Calcination for preparing the catalyst from the starting materials or for activating the catalyst is carried out at a temperature of usually 300° to 900° C., preferably 450° to 700° C., for a period of about 4 to about 16 hours while flowing a gas containing molecular oxygen. If desired, primary calcination may be carried out at a lower temperature than the aforesaid calcination temperature, and then calcination may be effected at the aforesaid temperature.

Typically, the catalyst of this invention can be prepared by adding aqueous solutions of a salt of the element of the component X, a chromium salt, a nickel salt, a bismuth salt and a salt of the element of the component Y to an aqueous solution of ammonium molybdate, adjusting the pH of the mixed solution to 2 to 9 with an aqueous solution of ammonia or an aqueous solution of nitric acid, stirring the mixture, drying the slurry after, if desired, adding a suitable carrier material thereto, drying the resulting cake-like material in the air, and calcining it at the aforesaid calcination temperature.

The catalyst of this invention may be used directly, or after it is diluted with a powdery, sol-like or gel-like carrier (diluent). The carrier or diluent may be those known in the art, for example titanium dioxide, silica gel, silica sol, diatomaceous earth, silicon carbide, alumina, pumice, silica-alumina, bentonite, zirconia, zeolite, talc, and refractories. Carriers containing silicon are preferred. The amount of the carrier may be selected properly. The catalyst may be used in the form of a powder or tablets or in other suitable shapes in a fixed bed, a moving bed or fluidized bed.

The reaction of the monolefin with molecular oxygen is carried out in a customary manner except that the novel catalyst described above is used. For example, a source of supply of molecular oxygen needs not to be highly pure oxygen, and rather air is suitable in industrial practice. If desired, the molecular oxygen may be diluted with an inert gas which does not adversely affect the reaction (for example, steam, nitrogen, argon, carbon dioxide gas, or a waste gas left after removal of hydrocarbons from the reaction products). The reaction temperature of 250° to 700° C., preferably 300° to 600° C., and the reaction pressure is normal atmospheric pressure to 10 atmospheres. The space velocity (SV) of the entire feed gases is 200 to 10000 hr$^{-1}$, preferably 300 to 6000 hr$^{-1}$ (STP). The concentration of the monolefin in the feed gas is 0.5 to 25% by volume. The ratio of monolefin to oxygen is 1:0.5–7. The preferred feed gas composition is monolefin:air:stream=1:3–30:0–50 (mole ratio).

According to this invention, conjugated diolefins such as 1,3-butadiene, isoprene, 1,3-pentadiene, and 2,3-dimethylbutadiene can be efficiently synthesized from the corresponding monolefins such as n-butene, isopentene, n-pentene and 2,3-dimethylbutene. The catalyst in accordance with this invention shows little variations in activity depending upon the types of the isomers of monolefin, nor is reduced in activity by paraffines. Accordingly, even when it is applied to a fraction industrially available at low cost, such as an isomeric mixture of a monolefin, or a mixture of such isomers and paraffins as a starting material, the corresponding conjugated diolefins can be obtained in equivalent yields to the case of using a single isomer of a monolefin as a starting material. Furthermore, since the catalyst in accordance with this invention has a long active lifetime and increasing of its strength does not adversely affect its activity, the reaction can be performed stably over a long period of time. The catalyst of this invention also has the advantage that it does not reduce the yield of the conjugated diolefin even when the concentration of the monolefin is increased and the space velocity is increased.

The following Examples illustrate the present invention more specifically. In these Examples, the conversion, selectivity and one-pass yield were calculated in accordance with the following equations. In calculation, if the corresponding conjugated diolefin is present in the starting monolefin, the amount of it is subtracted from the amount of the conjugated diolefin formed as a result of the reaction. A partially isomerized monolefin is regarded as the unreacted monolefin.

$$\text{Conversion of monolefin (\%)} = \frac{\text{Monolefin reacted (mole)}}{\text{Monolefin fed (mole)}} \times 100$$

$$\text{One-pass yield of dilefin} = \frac{\text{Corresponding diolefin formed (mole)}}{\text{Monolefin fed (mole)}} \times 100$$

$$\text{Selectivity of diolefin (\%)} = \frac{\text{Corresponding conjugated diolefin formed (mole)}}{\text{Monolefin reacted (mole)}} \times 100$$

EXAMPLE 1

Bismuth nitrate (48.5 g), 232.6 g of nickel nitrate, 45.6 g of chromium nitrate and 2.02 g of potassium nitrate were added to 150 ml of water and the mixture was heated to form a solution (referred to as solution A).

Lead nitrate (16.6 g) was added to 200 ml of water, and the mixture was heated to form a solution (to be referred to as solution B).

Ammonium molybdate (212 g) was dissolved in 400 ml of hot water to form a solution (referred to as solution C).

Solution B was added to solution A, and the mixture was fully stirred under heat. Then, solution C was added, and the mixture was vigorously stirred. A 3% by weight aqueous solution of ammonia was added to the mixture to adjust its pH to 5, and the mixture was evaporated to dryness over an oil bath. The solid product was dried at 120° C. for 8 hours, and primarily calcined at 350° C. for 4 hours in the air. The calcined product was pulverized to a size smaller than 100 mesh, and then to the pulverized product were added 40% by weight, based on the pulverized product, of a silicon carbide powder (smaller than 100 mesh), and 3% by weight, based on the pulverized product, of silica (20% by weight of silica sol), and further a suitable amount of a lubricant (a hot water solution of methyl cellulose and ethylene glycol). They were fully kneaded by a grinder until the mixture became uniform. The kneaded mixture was extruded into pellets having a diameter of 3 mm and a thickness of 1 cm, and dried at 120° C. for 16 hours. The dried mixture was then calcined in the air at 400° C. for 2 hours and further at 550° C. for 6 hours. The resulting catalyst can be expressed by the following composition formula excepting oxygen and the carrier.

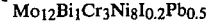

$Mo_{12}Bi_1Cr_3Ni_8I_{0.2}Pb_{0.5}$

The resulting catalyst is designated as [Catalyst No. (1)].

75 ml of the resulting catalyst No. (1) was packed into a stainless steel reaction tube having an inside diameter of 2.5 cm and a length to 60 cm, and heated to 350° C. over a metal bath. A starting hydrocarbon mixture having each of the compositions shown in Table 1 was passed through the catalyst layer so that the flow rate of n-butene (butene-1 plus trans-butene-2 plus cis-butene-2) contained therein became 18 liters/hour (gaseous state, NTP) and the flow rate of the air was 132 liters/hour (NTP). The results obtained five hours after the initiation of the reaction are shown in Table 2.

The results given in Table 2 show that when the catalyst of this invention is used, there is scarcely any difference between the reactivity of butene-1 and that of butene-2, and both give 1,3-butadiene in high yields. The results also show that even when BBRR available industrially at low cost and in great quantities is used as a starting material, the yield obtained is equivalent to that obtained when high purity butene is used. This is a very unique phenomenon.

phorus, and nitrate salts were used as sources of the other elements of X.

BBRR-1 having the composition shown in Table 1 was reacted in the same way as in Example 1 using the each of the catalyst prepared. The results obtained 5 hours after the initiation of the reaction are shown in Table 3 (the catalyst composition is shown by omitting oxygen and the carrier).

TABLE 3

| Run No. | Catalyst No. | Catalyst composition (atomic ratio) | Conversion of n-butene (%) | Yield (and selectivity) of 1,3-butadiene (%) |
|---|---|---|---|---|
| 2-1 | (2) | $Mo_{12}Bi_1Cr_3Ni_8Li_2Pb_{0.5}$ | 90.6 | 80.7 (89.1) |
| 2-2 | (3) | $Mo_{12}Bi_1Cr_4Ni_7Na_{0.7}Pb_{0.5}$ | 91.1 | 80.5 (88.4) |
| 2-3 | (4) | $Mo_{12}Bi_1Cr_3Ni_8Rb_{0.1}Pb_{0.5}$ | 94.6 | 85.2 (90.1) |
| 2-4 | (5) | $Mo_{12}Bi_1Cr_2Ni_9Cs_{0.05}Pb_{0.5}$ | 95.8 | 86.0 (89.8) |
| 2-5 | (6) | $Mo_{12}Bi_{4.8}Cr_{12}Ni_6Tl_{0.12}Pb_{0.5}$ | 94.4 | 83.8 (88.8) |
| 2-6 | (7) | $Mo_{12}Bi_4Cr_3Ni_8P_{0.5}Pb_1$ | 93.8 | 84.9 (90.5) |
| 2-7 | (8) | $Mo_{12}Bi_1Cr_3Ni_7P_{0.5}K_{0.1}Pb_{0.5}$ | 92.5 | 85.1 (92.0) |
| 2-8 | (9) | $Mo_{12}Bi_{0.5}Cr_7Ni_3P_1Cs_{0.1}Pb_2$ | 95.9 | 86.4 (90.1) |
| 2-9 | (10) | $Mo_{12}Bi_2Cr_2Ni_9K_{0.1}Tl_{0.1}Pb_{0.5}$ | 91.7 | 84.0 (91.6) |

TABLE 1

| Components (mole %) | Starting hydrocarbons | | | | | |
|---|---|---|---|---|---|---|
| | Butene-1 | trans-Butene-2 | cis-Butene-2 | n-Butene | BBRR-1 | BBRR-2 |
| Ethane | | | | | 0.25 | |
| Propane | | | | | 0.04 | 0.14 |
| Propylene | | | | | 0.01 | 0.06 |
| Allene | | | | | 0.01 | |
| Cyclopropane | | | | | 0.02 | |
| iso-Butane | 0.39 | | | 0.23 | 11.70 | 10.09 |
| n-Butene | 0.47 | 0.15 | | 0.35 | 13.49 | 32.41 |
| Butene-1 | 95.92 | | | 49.11 | 39.56 | 6.75 |
| iso-Butene | 0.09 | | | 0.05 | 1.24 | 0.45 |
| trans-Butene-2 | 0.55 | 99.08 | 0.23 | 25.01 | 17.44 | 34.97 |
| cis-Butene-2 | 1.87 | 0.44 | 99.72 | 24.60 | 13.91 | 8.88 |
| 1,3-Butadiene | 0.71 | 0.29 | 0.05 | 0.65 | 0.10 | 1.06 |
| $C_5$ or higher | | 0.04 | | | 1.99 | 4.15 |
| Others | | | | | 0.24 | 1.04 |
| Total | 100.00 | 100.00 | 100.00 | 100.00 | 100.00 | 100.00 |

TABLE 2

| Run No. | Starting hydrocarbon | Conversion of n-butene (%) | Yield (and selectivity) of 1,3-butadiene (%) |
|---|---|---|---|
| 1-1 | Butene-1 | 95.7 | 86.4 (90.3) |
| 1-2 | trans-Butene-2 | 94.1 | 85.7 (91.1) |
| 1-3 | cis-Butene-2 | 93.8 | 85.5 (91.2) |
| 1-4 | n-Butene | 95.3 | 86.1 (90.3) |
| 1-5 | BBRR-1 | 94.5 | 85.5 (90.5) |
| 1-6 | BBRR-2 | 94.0 | 85.2 (90.6) |

EXAMPLE 2

Catalysts No. (2) to No. (10) shown in Table 3 were prepared in the same way as in Example 1 except that various elements X were used instead of potassium and the catalyst composition was varied as shown in Table 3. 85% Phosphoric acid was used as a source of phos-

COMPARATIVE EXAMPLE 1

Comparative catalysts Nos. (c-1), (c-2) and (c-3) were prepared in the same way as in the preparation of the catalysts Nos. (1), (6) and (8) except that lead nitrate as component Y was not used.

Comparative catalysts Nos. (c-4) and (c-5) were also prepared in the same way as in the preparation of the catalyst No. (1) except that 40.4 g of ferric nitrate was added to solution A, and 45.6 g of chromium nitrate in solution A was replaced by 121.2 g of ferric nitrate.

Butene-1, trans-butene-2 and BBRR-1 having the compositions shown in Table 1 were each oxidatively hydrogenated in the same way as in Example 1 using each of the catalysts prepared as above. The results obtained 5 hours after the initiation of the reaction are shown in Table 4 (the catalyst compositions are indicated by excluding oxygen and the carrier).

TABLE 4

| Comparative catalyst | Catalyst composition (atomic ratio) | Reaction of butene-1 | | Reaction of trans-butene-2 | | Reaction of BBRR-1 | |
|---|---|---|---|---|---|---|---|
| | | Conversion of butene-1 (%) | Yield (and selectivity) of 1,3-butadiene | Conversion of trans-butene-2 (%) | Yield (and selectivity) of 1,3-butadiene | Conversion of n-butene | Yield (and selectivity) of 1,3-butadiene |
| (c-1) | $Mo_{12}Bi_1Cr_3Ni_8K_{0.2}$ | 88.8 | 74.6 (84.0) | 74.3 | 62.1 (83.6) | 80.4 | 64.1 (79.7) |
| (c-2) | $Mo_{12}Bi_{4.8}Cr_{1.2}Ni_6Tl_{0.12}$ | 79.4 | 62.6 (78.8) | 60.1 | 48.3 (80.4) | 64.7 | 50.3 (77.7) |
| (c-3) | $Mo_{12}Bi_1Cr_3Ni_7P_{0.5}K_{0.1}$ | 84.6 | 65.0 (76.8) | 67.2 | 52.9 (78.7) | 73.2 | 52.6 (71.9) |

TABLE 4-continued

| Comparative catalyst | Catalyst composition (atomic ratio) | Reaction of butene-1 | | Reaction of trans-butene-2 | | Reaction of BBRR-1 | |
|---|---|---|---|---|---|---|---|
| | | Conversion of butene-1 (%) | Yield (and selectivity) of 1,3-butadiene | Conversion of trans-butene-2 (%) | Yield (and selectivity) of 1,3-butadiene | Conversion of n-butene | Yield (and selectivity) of 1,3-butadiene |
| (c-4) | $Mo_{12}Bi_1Cr_3Ni_8K_{0.2}Pb_{0.5}Fe_1$ | 94.5 | 79.7 (84.3) | 75.8 | 63.0 (83.1) | 83.6 | 65.5 (78.3) |
| (c-5) | $Mo_{12}Bi_1Fe_3Ni_8K_{0.2}Pb_{0.5}$ | 80.4 | 60.1 (74.8) | 52.5 | 42.5 (81.0) | 60.1 | 42.0 (70.0) |

The results given in Table 4 demonstrate that when the catalyst system not containing Pb and the catalyst containing Fe are used, the reactivity of butene-2 is inferior, and therefore when these catalysts are used in the oxidative dehydrogenation of BBRR which is industrially available in great quantities at low cost, no satisfactory yield of butadiene is obtained.

EXAMPLE 3

Catalysts shown in Table 5 were prepared in the same way as in Examples 1 and 2 except that the types and amounts of components X and Y were changed. As sources of component X, 85% phosphoric acid was used for phosphorus, and nitrates were used for the other elements. As sources of component Y, nitrate salts were used for Al, Ga, Zr, Pb and Mn (an aqueous solution of each of these was used as solution B), and finely divided oxides were used for Nb, Ta and Hf (a suspension of each of these in warm water was used as solution B).

BBRR-1 was oxidatively dehydrogenated in the same way as in Example 1 using each of the catalysts so prepared. The results obtained 5 hours after the initiation of the reaction are shown in Table 5 (the catalyst compositions are shown by omitting oxygen and the carrier).

the unreacted oxygen and by-products carbon monoxide and carbon dioxide as well as nitrogen, the results obtained 5 hours after the reaction were as follows:
Conversion of n-butene: 95.8%
Yield of 1,3-butadiene: 86.3%
Selectivity of 1,3-butadiene: 90.1%

EXAMPLE 6

The same reaction as in Run No. 1-5 of Example 1 was performed, and even after the lapse of 5 hours, was continued to test the lifetime of the catalyst. At the end of 4000 hours, the conversion of n-butene in BBRR-1 was 94.0%; the yield of 1,3-butadiene was 85.4%; and the selectivity of 1,3-butadiene was 90.9%.

The activity of the catalyst determined at the end of 4000 hours was substantially the same as that at the initiation of the reaction.

During the reaction period, the constituents and proportions of the fed BBRR-1 considerably varied every time a fresh supply of the material was fed. But the reaction proceeded always stably, and the reaction results were substantially constant.

COMPARATIVE EXAMPLE 2

The oxidative dehydrogenation of BBRR-1 with the

TABLE 5

| Run No. | Catalyst No. | Catalyst composition (atomic ratio) | Conversion of n-butene (%) | Yield (and selectivity) of 1,3-butadiene |
|---|---|---|---|---|
| 3-1 | (11) | $Mo_{12}Bi_1Cr_3Ni_8K_{0.2}Mn_{0.5}$ | 93.6 | 83.8 (89.5) |
| 3-2 | (12) | $Mo_{12}Bi_6Cr_{0.5}Ni_7K_{0.5}Al_3$ | 94.7 | 85.8 (90.6) |
| 3-3 | (13) | $Mo_{12}Bi_1Cr_2Ni_9K_{0.2}Ga_1$ | 90.1 | 81.4 (90.3) |
| 3-4 | (14) | $Mo_{12}Bi_{0.5}Cr_3Ni_8K_{0.2}Zr_{0.5}$ | 92.5 | 84.3 (91.1) |
| 3-5 | (15) | $Mo_{12}Bi_1Cr_4Ni_7Tl_{0.2}Nb_{0.5}$ | 91.0 | 81.3 (89.3) |
| 3-6 | (16) | $Mo_{12}Bi_1Cr_3Ni_8Li_6Ta_{10}$ | 91.0 | 80.8 (88.8) |
| 3-7 | (17) | $Mo_{12}Bi_1Cr_2Ni_9Na_2Hf_4$ | 95.3 | 80.7 (84.7) |
| 3-8 | (18) | $Mo_{12}Bi_1Cr_3Ni_7P_{0.1}Rb_{0.1}Mn_1$ | 94.4 | 84.9 (89.9) |
| 3-9 | (19) | $Mo_{12}Bi_1Cr_2Ni_8Cs_{0.03}Pb_{0.2}Zr_{0.3}$ | 94.8 | 85.0 (89.7) |
| 3-10 | (20) | $Mo_{12}Bi_1Cr_3Ni_8P_{0.5}Tl_{0.1}Nb_1$ | 93.2 | 81.7 (87.7) |
| 3-11 | (21) | $Mo_{12}Bi_1Cr_3Ni_4Li_3Ta_7Hf_1$ | 90.9 | 80.6 (88.7) |

EXAMPLE 4

Fifty milliliters of the catalyst obtained in Example 1 was packed into a stainless steel reaction tube having an inside diameter of 2.5 cm and a length of 60 cm, and heated to 360° C. over a metal bath. A feed gas consisting of BBRR-1, air and steam in a mole ratio of 15:53:32 was passed through the catalyst for a contact time of 1 second (NTP). Five hours after the initiation of the reaction, the conversion of n-butene contained in BBRR-1 was 96.5%; the yield of 1,3-butadiene was 86.8%; and the selectivity of 1,3-butadiene was 89.9%.

EXAMPLE 5

The same reaction as in Example 4 was performed except that a waste gas left after removal of hydrocarbons from the reaction products was used instead of steam. In spite of the fact that the waste gas contained comparative catalyst No. (c-1) in Comparative Example 1 was continued, after the lapse of 5 hours, to test the lifetime of the catalyst. At the end of 4000 hours, the conversion of n-butene in BBRR-1 was decreased to 55.3%; the yield of 1,3-butadiene was decreased to 43.6%; and the selectivity of 1,3-butadiene was decreased to 78.8%.

During the reaction period, the results of the reaction considerably varied owing to the variations in the constituents and proportions of the fed BBRR-1 every time a fresh supply of the starting material was fed. The reaction, too, was unstable.

EXAMPLE 7

The same reaction as in Example 1 was carried out except that a hydrocarbon mixture containing n-pentene (pentene-1 and pentene-2) and isoprene (3-methylbutene-1, 2-methylbutene-1 and 2-methyl-butene-2) was used, and the feed gas was passed through the catalyst layer such that the flow rate of the n-pentene and isopentene combined was 18 liters/hour (gaseous state; NTP) and the flow rate of the air was 132 liters/hour (NTP).

Five hours after the initiation of the reaction, the conversion of isopentene was 80.6%; the yield of isoprene was 66.8%; and the selectivity of isoprene was 82.9%. The conversion of n-pentene was 82.2%; the yield of 1,3-pentadiene was 69.6%; and the selectivity of 1,3-pentadiene was 84.7%.

TABLE 6

| Component | Composition (% by weight) | Component | Composition (% by weight) |
|---|---|---|---|
| iso-Pentane | 8.7 | 1,4-Pentadiene | 2.0 |
| 3-Methyl-butene-1 | 1.5 | 2-Methyl-butene-2 | 8.0 |
| n-Pentane | 36.4 | isoprene | 0.4 |
| Pentene-1 | 10.1 | Cyclopentadiene | 0.9 |
| 2-Methyl-butene-1 | 17.1 | Others | 1.4 |
| trans-Pentene-2 | 8.1 | | |
| cis-Pentene-2 | 5.4 | | |

COMPARATIVE EXAMPLE 3

The same reaction as in Example 7 was carried out except that the comparative catalyst No. (c-1) was used as the catalyst. Five hours after the initiation of the reaction, the results were as follows:

Conversion for isopentene: 62.5%
Yield of isoprene: 41.3%
Selectivity of isoprene: 66.1%
Conversion of n-pentene: 64.0%
Yield of 1,3-pentadiene: 42.6%
Selectivity of 1,3-pentadiene: 66.6%

What we claim is:

1. In a process for producing a conjugated diolefin which comprises oxidatively dehydrogenating a monolefin having at least 4 carbon atoms in the vapor phase with molecular oxygen to form the corresponding conjugated diolefin; the improvement wherein the oxidative dehydrogenation is carried out in the presence of a catalyst having the general composition formula $$Mo_aBi_bCr_cNi_dX_eY_fO_g$$

wherein X represents at least one element selected from Li, Na, K, Rb, Cs, Tl and P, Y represents at least one element selected from Al, Ga, Zr, Pb, Nb, Ta, Hf and Mn, and a, b, c, d, e, f and g respectively represent the number of Mo, Bi, Cr, Ni, X, Y and O atoms, and when a=12, b=0.05–20, c=0.05–20, d=0.1–30, e=0.01–10, f=0.01–20, and g is the number of oxygen atoms which satisfies the atomic valences of the other elements.

2. The process of claim 1 wherein when a=12, b=0.1–8, c=0.1–10, d=1–20, e=0.01–5, f=0.05–10, and g is the number of oxygen atoms which satisfies the atomic valences of the other elements.

3. The process of claim 1 wherein the monolefin has 4 to 6 carbon atoms.

4. The process of claim 3 wherein the monolefin is n-butene, isopentene, or n-pentene.

5. The process of claim 1 wherein the oxidative dehydrogenation is carried out at a temperature of 250° to 700° C.

6. In a process for producing a conjugated diolefin from a mixture of monomeric monolefin isomers of a monolefin having 4 to 6 carbon atoms by oxidatively dehydrogenating the monomer mixture in the vapor phase at a temperature of 250° C. to 700° C. with molecular oxygen in the presence of a catalytic oxide, the improvement wherein the catalytic oxide consists essentially of the elements molybdenum, bismuth, chromium, nickel, at least one element X, and at least one element Y, wherein X represents Li, Na, K, Rb, Cs, Tl or P and Y represents Al, Ga, Zr, Pb, Nb, Ta, Hf or Mn, said catalytic oxide having the formula $$Mo_aBi_bCr_cNi_dX_eY_fO_g$$

wherein a, b, c, d, e, f and g respectively represent the number of Mo, Bi, Cr, Ni, X, Y, and O atoms, and when a=12, b=0.5–20, c=0.05–20, d=0.1–30, e=0.01–10, f=0.01–20, and g is the number of oxygen atoms which satisfies the atomic valences of the other elements, whereby each of the monolefin isomers of said mixture is converted to the corresponding conjugated diolefin at substantially the same yields as would be obtained if only a single monolefin isomer was present.

7. The process of claim 6 wherein when a=12, b=0.1–8, c=0.1–10, d=1–20, e=0.01–5, f=0.05–10, and g is the number of oxygen atoms which satisfies the atomic valences of the other elements.

* * * * *